(12) United States Patent
Champagne et al.

(10) Patent No.: US 10,194,923 B2
(45) Date of Patent: Feb. 5, 2019

(54) TOOL FOR PERCUTANEOUS JOINT CARTILAGE DESTRUCTION AND PREPARATION FOR JOINT FUSION

(71) Applicant: Exsomed International IP, LLC, Avarua, Rarotonga (CK)

(72) Inventors: Lloyd P. Champagne, Phoenix, AZ (US); Jozef Zoldos, Phoenix, AZ (US); Atilla A Hunson, Phoenix, AZ (US)

( * ) Notice: Subject to any disclaimer, the term of this patent is extended or adjusted under 35 U.S.C. 154(b) by 116 days.

(21) Appl. No.: 15/151,252

(22) Filed: May 10, 2016

(65) Prior Publication Data

US 2017/0325827 A1  Nov. 16, 2017

(51) Int. Cl.
*A61B 17/16* (2006.01)

(52) U.S. Cl.
CPC .......... *A61B 17/1659* (2013.01); *A61B 17/16* (2013.01); *A61B 17/164* (2013.01); *A61B 17/1604* (2013.01); *A61B 17/1615* (2013.01); *A61B 17/1637* (2013.01); *A61B 17/1662* (2013.01); *A61B 17/1682* (2013.01)

(58) Field of Classification Search
CPC ... A61B 17/16; A61B 17/1604; A61B 17/164; A61B 17/1659; A61B 17/1662; A61B 17/1682
See application file for complete search history.

(56) References Cited

U.S. PATENT DOCUMENTS

| | | | |
|---|---|---|---|
| 1,741,279 A | 12/1929 | Bowman | |
| 2,037,586 A | 4/1936 | Olson | |
| 2,210,455 A | 8/1940 | Hosking | |
| 2,217,951 A | 10/1940 | Hosking | |
| 2,229,892 A | 1/1941 | Hosking | |
| 2,242,003 A | 5/1941 | Lorenzo | |
| 3,275,055 A | 9/1966 | Gutshall | |
| 3,397,699 A | 8/1968 | Kohl | |
| 3,717,146 A | 2/1973 | Halloran | |

(Continued)

FOREIGN PATENT DOCUMENTS

| | | |
|---|---|---|
| CH | 643131 | 5/1984 |
| CH | 646858 | 12/1984 |

(Continued)

OTHER PUBLICATIONS

USPTO; Non-Final Office Action dated Nov. 4, 2016 in U.S. Appl. No. 14/503,119.

(Continued)

*Primary Examiner* — Larry E Waggle, Jr.
(74) *Attorney, Agent, or Firm* — Snell & Wilmer L.L.P.

(57) ABSTRACT

A tool for scrubbing, removing tissue from the medullary cavity or joint cavity of a bone or removing cartilage and/or cortical bone from a joint cavity has a proximal end, a distal end, and a cannula extending therethrough. The distal end includes at least one scraping surface and/or cutting surface to soften marrow in the medullary cavity or joint cavity as the scraping and/or cutting surface(s) are rotated or otherwise moved relative to the medullary cavity or joint cavity. When used, the tool may be attached to a drill and the cannula receives a K-wire previously inserted into the medullary or joint cavity. The drill rotates the tool around the K-wire and pushes the tool over the K-wire into the medullary cavity or joint cavity.

24 Claims, 3 Drawing Sheets

(56) References Cited

U.S. PATENT DOCUMENTS

| | | | |
|---|---|---|---|
| 4,016,874 A | 4/1977 | Maffei | |
| 4,175,555 A | 11/1979 | Herbert | |
| 4,380,414 A | 4/1983 | Capuano | |
| 4,463,753 A | 8/1984 | Gustilo | |
| 4,471,777 A | 9/1984 | McCorkle | |
| 4,584,722 A | 4/1986 | Levy et al. | |
| 4,608,965 A | 9/1986 | Anspach | |
| 4,764,066 A | 8/1988 | Terrell | |
| 4,781,191 A | 11/1988 | Thompson | |
| 4,812,095 A | 3/1989 | Piacenti | |
| 4,901,717 A | 2/1990 | Moore et al. | |
| 4,909,789 A | 3/1990 | Taguchi et al. | |
| 5,061,283 A | 10/1991 | Silvestrini | |
| 5,234,299 A | 8/1993 | Giannuzzi | |
| 5,312,255 A | 5/1994 | Bauer | |
| 5,345,927 A | 9/1994 | Bonutti | |
| 5,443,466 A | 8/1995 | Shah | |
| 5,645,545 A * | 7/1997 | Bryant | A61B 17/72 606/170 |
| 5,667,510 A | 9/1997 | Combs | |
| 5,690,633 A | 11/1997 | Taylor et al. | |
| 5,853,413 A | 12/1998 | Carter et al. | |
| 6,187,007 B1 | 2/2001 | Frigg | |
| 6,221,006 B1 | 4/2001 | Dubrul et al. | |
| 6,306,140 B1 | 10/2001 | Siddiqui | |
| 6,475,242 B1 | 11/2002 | Bramlet | |
| 6,517,541 B1 | 2/2003 | Sesic | |
| 6,592,623 B1 | 7/2003 | Bowlin et al. | |
| 6,607,530 B1 | 8/2003 | Carl et al. | |
| 6,808,526 B1 | 10/2004 | Magerl et al. | |
| 7,041,106 B1 | 5/2006 | Carver et al. | |
| 7,334,976 B2 | 2/2008 | Dicke | |
| 7,465,135 B2 | 12/2008 | Fritsch | |
| 7,507,242 B2 * | 3/2009 | Triplett | A61B 17/1671 606/87 |
| 7,708,738 B2 | 5/2010 | Fourcault et al. | |
| 7,766,942 B2 | 8/2010 | Patterson | |
| 7,988,724 B2 | 8/2011 | Salahieh et al. | |
| 8,011,866 B2 | 9/2011 | Harris | |
| 8,157,803 B1 | 4/2012 | Zirkle, Jr. | |
| 8,398,687 B2 | 3/2013 | Vasta et al. | |
| 8,414,648 B2 * | 4/2013 | Reiley | A61B 17/1615 606/246 |
| 8,419,776 B2 | 4/2013 | Prandi et al. | |
| 8,518,042 B2 | 8/2013 | Winsow et al. | |
| 8,568,462 B2 | 10/2013 | Sixto et al. | |
| 8,597,337 B2 | 12/2013 | Champagne | |
| 8,608,783 B2 | 12/2013 | Graham et al. | |
| 8,814,918 B2 | 8/2014 | Orbay et al. | |
| 8,852,253 B2 | 10/2014 | Mafi | |
| 8,864,804 B2 | 10/2014 | Champagne et al. | |
| 8,888,429 B2 | 11/2014 | Pamer | |
| 8,906,075 B2 | 12/2014 | Conley et al. | |
| 9,017,404 B2 | 4/2015 | Champagne et al. | |
| 9,046,120 B2 | 6/2015 | Phua | |
| 9,175,715 B2 | 11/2015 | Babej | |
| 9,265,600 B2 | 2/2016 | Niese | |
| 9,480,515 B2 | 11/2016 | Champagne | |
| 9,539,084 B2 | 1/2017 | Champagne | |
| 10,098,680 B2 | 10/2018 | Champagne | |
| 2001/0049529 A1 | 12/2001 | Cachia et al. | |
| 2002/0055747 A1 | 5/2002 | Cano et al. | |
| 2002/0055749 A1 | 5/2002 | Esnouf et al. | |
| 2002/0198527 A1 | 12/2002 | Muckter | |
| 2003/0014077 A1 | 1/2003 | Leung | |
| 2003/0130735 A1 | 7/2003 | Rogalski | |
| 2004/0193217 A1 | 9/2004 | Lubbers | |
| 2004/0210227 A1 | 10/2004 | Trail et al. | |
| 2004/0260288 A1 | 12/2004 | Means | |
| 2005/0075642 A1 | 4/2005 | Felt et al. | |
| 2005/0085824 A1 | 4/2005 | Castaneda | |
| 2005/0107791 A1 | 5/2005 | Manderson | |
| 2005/0143735 A1 | 6/2005 | Kyle | |
| 2006/0129153 A1 | 6/2006 | Klaue et al. | |
| 2006/0149249 A1 | 7/2006 | Mathoulin et al. | |
| 2006/0165506 A1 | 7/2006 | Panasik | |
| 2006/0195099 A1 | 8/2006 | Bottlang | |
| 2006/0271061 A1 | 11/2006 | Beyar | |
| 2006/0276790 A1 | 12/2006 | Dawson | |
| 2007/0027547 A1 | 2/2007 | Rydell et al. | |
| 2007/0135816 A1 | 6/2007 | Kropf et al. | |
| 2007/0282342 A1 | 12/2007 | Niederberger et al. | |
| 2007/0299449 A1 | 12/2007 | Allinniemi et al. | |
| 2008/0183220 A1 | 7/2008 | Glazer | |
| 2008/0219801 A1 | 9/2008 | Toenjes | |
| 2008/0249547 A1 | 10/2008 | Dunn | |
| 2008/0249574 A1 | 10/2008 | McCombs et al. | |
| 2009/0062868 A1 | 3/2009 | Casutt | |
| 2009/0299369 A1 | 12/2009 | Orbay et al. | |
| 2010/0106254 A1 | 4/2010 | Delsignore | |
| 2010/0121136 A1 | 5/2010 | Champagne | |
| 2010/0211115 A1 | 8/2010 | Tyber et al. | |
| 2010/0324556 A1 | 12/2010 | Tyber et al. | |
| 2011/0009865 A1 | 1/2011 | Offaly | |
| 2011/0130794 A1 | 6/2011 | Vaidya | |
| 2012/0083847 A1 | 4/2012 | Heubner et al. | |
| 2012/0136398 A1 | 5/2012 | Mobasser | |
| 2012/0191140 A1 | 7/2012 | Bonutti | |
| 2012/0221104 A1 | 8/2012 | Altman et al. | |
| 2012/0253464 A1 | 10/2012 | Hwang et al. | |
| 2012/0253465 A1 | 10/2012 | Missos | |
| 2013/0012987 A1 | 1/2013 | Klein et al. | |
| 2013/0053961 A1 | 2/2013 | Darwin et al. | |
| 2013/0060333 A1 | 3/2013 | Gonzalez | |
| 2013/0131699 A1 | 5/2013 | Jiang et al. | |
| 2013/0138123 A1 | 5/2013 | Stone et al. | |
| 2013/0190872 A1 | 7/2013 | Makower et al. | |
| 2013/0197592 A1 | 8/2013 | Mafi | |
| 2013/0245626 A1 | 9/2013 | Lavi et al. | |
| 2013/0245700 A1 | 9/2013 | Choinski | |
| 2013/0245762 A1 | 9/2013 | Van Kampen et al. | |
| 2013/0261662 A1 | 10/2013 | Mayer et al. | |
| 2013/0274879 A1 | 10/2013 | Champagne et al. | |
| 2013/0282058 A1 | 10/2013 | ElAttrache et al. | |
| 2013/0325011 A1 | 12/2013 | Cleveland et al. | |
| 2014/0025124 A1 | 1/2014 | Champagne et al. | |
| 2014/0067063 A1 | 3/2014 | Bonutti | |
| 2014/0257349 A1 | 9/2014 | Sudekum | |
| 2014/0276846 A1 * | 9/2014 | Mauldin | A61B 17/1664 606/80 |
| 2014/0336712 A1 | 11/2014 | Strnad et al. | |
| 2015/0066060 A1 | 3/2015 | Bojarski | |
| 2015/0094722 A1 | 4/2015 | Champagne et al. | |
| 2015/0094724 A1 | 4/2015 | Champagne et al. | |
| 2015/0094777 A1 | 4/2015 | Champagne et al. | |
| 2015/0173737 A1 | 6/2015 | Champagne et al. | |
| 2015/0182325 A1 | 7/2015 | Champagne et al. | |
| 2016/0030097 A1 | 2/2016 | Mildner | |
| 2016/0256290 A1 | 9/2016 | Seavey et al. | |
| 2016/0296263 A1 | 10/2016 | Champagne et al. | |
| 2016/0296264 A1 | 10/2016 | Champagne et al. | |
| 2016/0338748 A1 | 11/2016 | Champagne et al. | |
| 2017/0027577 A1 | 2/2017 | Kubiak et al. | |
| 2017/0035553 A1 | 2/2017 | Champagne et al. | |
| 2017/0049167 A1 | 2/2017 | Champagne et al. | |
| 2017/0189090 A1 | 7/2017 | Champagne et al. | |
| 2017/0196609 A1 | 7/2017 | Champagne et al. | |
| 2018/0021124 A1 | 1/2018 | Champagne et al. | |

FOREIGN PATENT DOCUMENTS

| | | |
|---|---|---|
| DE | 2713386 | 11/1978 |
| DE | 102007003645 | 7/2008 |
| DE | 202013101135 | 6/2014 |
| EP | 0597223 | 5/1994 |
| EP | 1378205 | 1/2004 |
| EP | 2606843 | 6/2013 |
| EP | 602013043888.9 | 9/2018 |
| GB | 2007099 | 5/1979 |
| GB | 2181356 | 4/1987 |
| WO | WO199733537 | 9/1997 |
| WO | WO2004093700 | 4/2004 |
| WO | WO2005092226 | 10/2005 |
| WO | WO2006105935 | 12/2006 |

(56) References Cited

FOREIGN PATENT DOCUMENTS

| WO | WO2007081601 | 7/2007 |
|---|---|---|
| WO | WO2007109140 | 9/2007 |
| WO | WO2008063156 | 5/2008 |
| WO | WO2010151589 | 12/2010 |
| WO | 2012050424 | 4/2012 |
| WO | WO2014011933 | 1/2014 |
| WO | 2014089522 | 6/2014 |
| WO | 2015050900 | 4/2015 |
| WO | WO2015050895 | 9/2015 |
| WO | WO2015050896 | 9/2015 |
| WO | WO2015050898 | 9/2015 |
| WO | WO2015050902 | 9/2015 |
| WO | 2016186847 | 11/2016 |

OTHER PUBLICATIONS

USPTO; Non-Final Office Action dated Jan. 27, 2017 in U.S. Appl. No. 14/503,157.
USPTO; Non-Final Office Action dated Feb. 9, 2017 in U.S. Appl. No. 14/503,228.
PCT; International Search Report and Written Opinion dated Sep. 30, 2014 in Application No. PCT/US2014/058472.
PCT; International Search Report and Written Opinion dated May 4, 2016 in Application No. PCT/US2016/030850.
USPTO; Non-Final Office Action dated Nov. 1, 2017 in U.S. Appl. No. 15/297,698.
USPTO; Non-Final Office Action dated Nov. 28, 2017 in U.S. Appl. No. 15/189,845.
USPTO; Non-Final Office Action dated Nov. 30, 2017 in U.S. Appl. No. 15/189,829.
USPTO; Requirement for Restriction dated Nov. 30, 2017 in U.S. Appl. No. 15/214,412.
USPTO; Non-Final Office Action dated Dec. 8, 2017 in U.S. Appl. No. 15/146,824.
USPTO; Non-Final Office Action dated Dec. 15, 2017 in U.S. Appl. No. 14/984,145.
USPTO; Non-Final Office Action dated Apr. 10, 2017 in U.S. Appl. No. 14/641,024.
USPTO; Final Office Action dated Jun. 2, 2017 in U.S. Appl. No. 14/503,157.
USPTO; Final Office Action dated Jun. 13, 2017 in U.S. Appl. No. 14/503,119.
USPTO; Final Office Action dated Aug. 31, 2017 in U.S. Appl. No. 14/503,228.
PCT; International Search Report and Written Opinion dated Sep. 17, 2010 in Application No. PCT/US2009/046662.
EP; Examination Report dated May 30, 2011 in Application No. EP 09774002.1.
USPTO; Office Action dated Oct. 4, 2011 in U.S. Appl. No. 12/372,712.
USPTO; Office Action dated Mar. 21, 2012 in U.S. Appl. No. 12/480,676.
EP; Examination Report dated May 25, 2012 in Application No. EP 09774002.1.
USPTO; Office Action dated May 29, 2012 in U.S. Appl. No. 12/372,712.
USPTO; Office Action dated Sep. 18, 2012 in U.S. Appl. No. 12/480,676.
USPTO; Office Action dated Mar. 22, 2013 in U.S. Appl. No. 12/372,712.
USPTO; Notice of Allowance dated Jul. 30, 2013 in U.S. Appl. No. 12/372,712.
PCT; International Search Report and Written Opinion dated Sep. 9, 2013 in Application No. PCT/US2013/050155.
USPTO; Office Action dated Sep. 24, 2013 in U.S. Appl. No. 12/480,676.
USPTO; Office Action dated Feb. 18, 2014 in U.S. Appl. No. 13/555,933.
USPTO; Notice of Allowance dated Jun. 25, 2014 in U.S. Appl. No. 13/555,933.
USPTO; Office Action dated Aug. 29, 2014 in U.S. Appl. No. 13/648,019.
PCT; International Search Report and Written Opinion dated Dec. 10, 2014 in Application No. PCT/US2014/058463.
PCT; International Search Report and Written Opinion dated Dec. 12, 2014 in Application No. PCT/US2014/058474.
USPTO; Notice of Allowance dated Dec. 31, 2014 in U.S. Appl. No. 13/648,019.
PCT; International Search Report and Written Opinion dated Jan. 20, 2015 in Application No. PCT/US2014/058448.
PCT; International Search Report and Written Opinion dated Feb. 9, 2015 in Application No. PCT/US2014/058441.
USPTO; Office Action dated Dec. 9, 2015 in U.S. Appl. No. 14/640,657.
USPTO; Office Action dated Sep. 22, 2015 in U.S. Appl. No. 14/503,228.
USPTO; Office Action dated Oct. 5, 2015 in U.S. Appl. No. 13/940,173.
USPTO; Final Office Action dated May 2, 2016 in U.S. Appl. No. 14/503,228.
USPTO; Final Office Action dated May 23, 2016 in U.S. Appl. No. 14/640,657.
USPTO; Final Office Action dated May 23, 2016 in U.S. Appl. No. 13/940,173.
USPTO; Notice of Allowance dated Jul. 1, 2016 in U.S. Appl. No. 13/940,173.
USPTO; Notice of Allowance dated Sep. 1, 2016 in U.S. Appl. No. 14/640,657.
EP; Examination Report dated Feb. 12, 2016 in Application No. EP 13742332.3.
EP; 2nd Examination Report dated Oct. 11, 2016 in Application No. EP 13742332.3.
EP; Notice of Allowance dated Apr. 12, 2018 in Application No. EP 13742332.3.
USPTO; Non-Final Office Action dated Jun. 6, 2018 in U.S. Appl. No. 14/503,228.
USPTO; Notice of Allowance dated Jun. 15, 2018 in U.S. Appl. No. 15/189,845.
USPTO; Final Office Action dated Jun. 26, 2018 in U.S. Appl. No. 14/984,145.
USPTO; Notice of Allowance dated Jul. 11, 2018 in U.S. Appl. No. 15/189,845.
USPTO; Final Office Action dated Jul. 20, 2018 in U.S. Appl. No. 14/993,972.
USPTO; Non-Final Office Action dated Feb. 27, 2018 in U.S. Appl. No. 14/503,157.
USPTO; Non-Final Office Action dated Mar. 5, 2018 in U.S. Appl. No. 14/993,972.
USPTO; Non-Final Office Action dated Mar. 5, 2018 in U.S. Appl. No. 15/214,412.
USPTO; Final Office Action dated Aug. 8, 2018 in U.S. Appl. No. 15/214,412.
USPTO; Final Office Action dated Oct. 17, 2018 in U.S. Appl. No. 15/146,824.

* cited by examiner

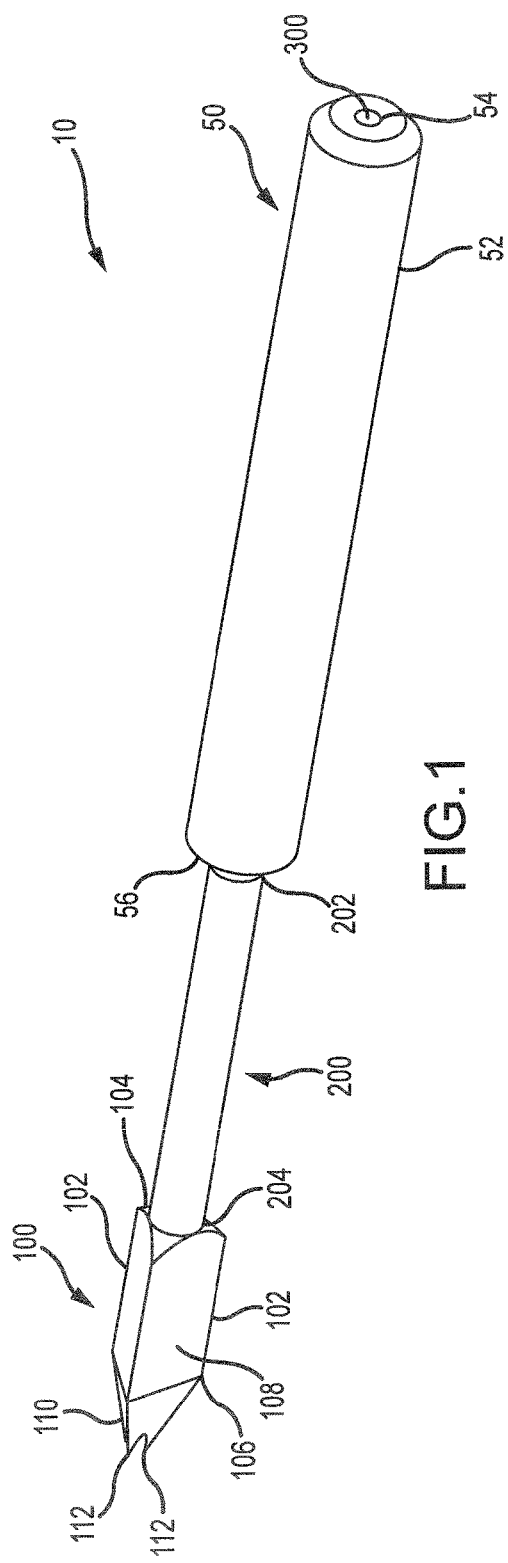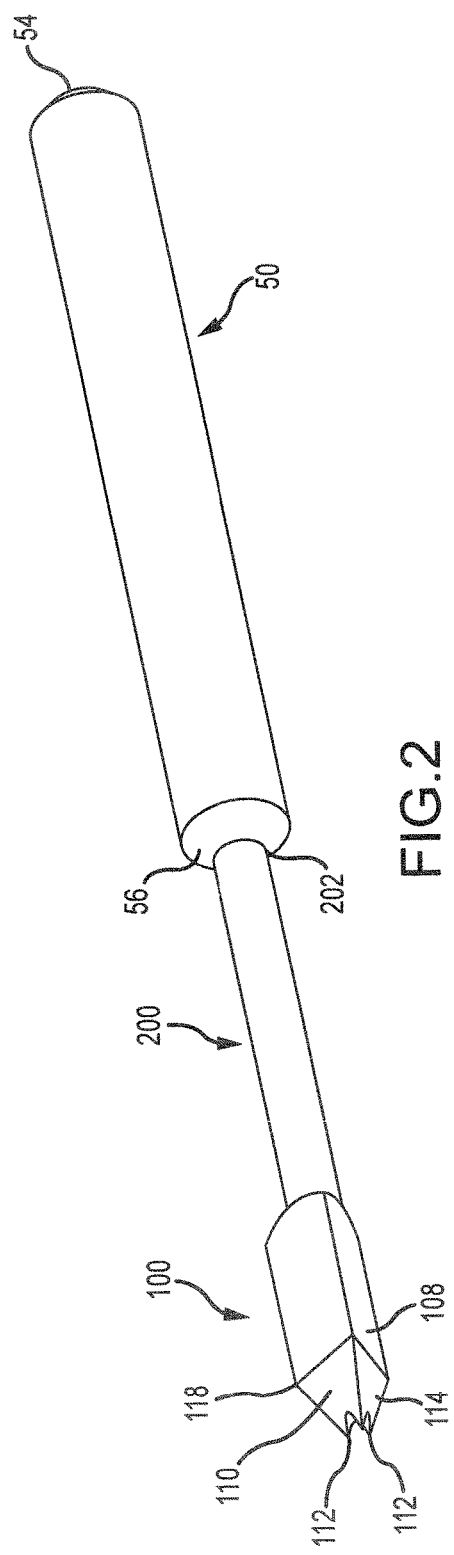

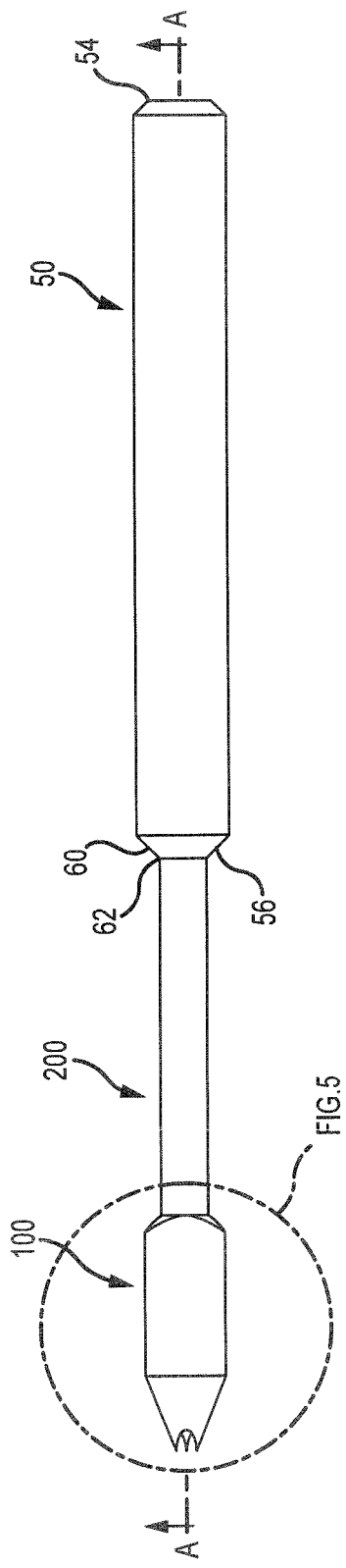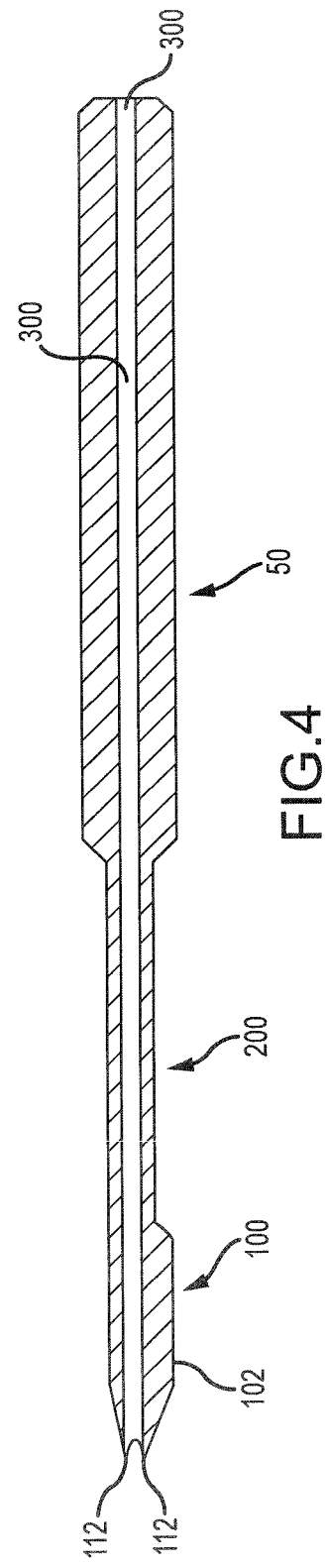

TOOL FOR PERCUTANEOUS JOINT CARTILAGE DESTRUCTION AND PREPARATION FOR JOINT FUSION

FIELD OF THE INVENTION

The present disclosure generally relates to medical devices. More particularly, the disclosure relates to tools suitable for preparing a joint for fusion with a percutaneous method of cartilage destruction.

BACKGROUND OF THE INVENTION

For various reasons, it may be desirable to destroy or remove cartilage from the joint area of a bone. For example, such procedures are often employed in the treatment of hand or foot injuries during the process of joint fusion to facilitate the healing of a joint fusion. Joint fusion is indicated for unstable or painful joints. The process of joint fusion involves removal or destruction of the smooth cartilage lining of a joint followed by fixation of the raw ends of the bone to each other with the intent to have the bone ends heal and form a solid, non-movable, bone construct that is no longer unstable or painful.

A typical method of performing joint cartilage removal involves creating and incision or open arthrotomy and mechanically removing the joint cartilage with a burr, or biting or cutting instrument. Usually a rongeur, a type of biting tool, is used. Sometimes in addition to cartilage, subcortical hard bone is also removed. Alternatively, destruction of the cartilage in some form as opposed to removal of cartilage may also be satisfactory. Although this technique works relatively well, the method is relatively cumbersome and time consuming, requiring a large exposure or access to the joint. Accordingly, improved techniques and tools for joint preparation and cartilage removal or destruction when fusions are performed are desired.

The present invention allows the safe insertion of a cartilage destroyer into a joint with percutaneous techniques. The guidewire controls the device preventing errant travel of the device and its sharp cutting edges providing for safe percutaneous cartilage destruction.

SUMMARY OF THE INVENTION

The present disclosure generally relates to tools and techniques for removing or destroying joint cartilage during joint fusion procedures. More particularly, the disclosure relates to tools that include one or more scraping and/or cutting surfaces to break up and/or destroy or remove cartilage in a joint and to methods of using the tools.

A tool for destroying or removing cartilage from bone includes a proximal end, a distal end, and a cannula extending through the tool. The distal end includes at least one scraping and/or cutting surface to break up and/or soften the cartilage in the joint as the scraping and/or cutting surface is rotated or otherwise moved within the cavity. The proximal end can include a section that can be received by a device, such as a drill, that can be used to cause the tool to rotate. The cannula can be configured to receive a guide wire, such as a K-wire, to help guide the distal end of the tool towards and into the joint cavity to be scrubbed or arthrolysed.

When used, the tool is preferably attached to a drill and the cannula has received an end of a guide wire, wherein a portion of the guide wire has been inserted into the joint cavity. The drill rotates the tool around the guide wire and can be used to push the tool over the guide wire and into the joint cavity. Once the tool is inserted into the joint cavity, the drill can be used to move the tool along an axis of the guide wire into the cavity as well as cause the tool to rotate within the cavity.

Procedures using a tool as described herein can be less cumbersome and less time consuming, less traumatic compared to traditional medullary cavity scrubbing techniques. The device as designed preferably provides a lead cutting surface suitable for trans-cutaneous or percutaneous insertion into a joint though a small skin hole The device being of a cannulated design allows for controlled delivery of the sharp cutting lead end of the device into and out of the joint, thus providing for cartilage destruction, but preventing creep of the device into other areas such as nerves and tendons

BRIEF DESCRIPTION OF THE DRAWINGS

FIG. 1 is a perspective, side view of a tool according to aspects of the invention.

FIG. 2 is a different, perspective, side view of the tool according to aspects of the invention.

FIG. 3 is a side view of the tool of FIGS. 1 and 2.

FIG. 4 is a cross-sectional side view of the tool of FIG. 3 taken along lines E-E.

DETAILED DESCRIPTION OF PREFERRED EMBODIMENTS

Figure 5:
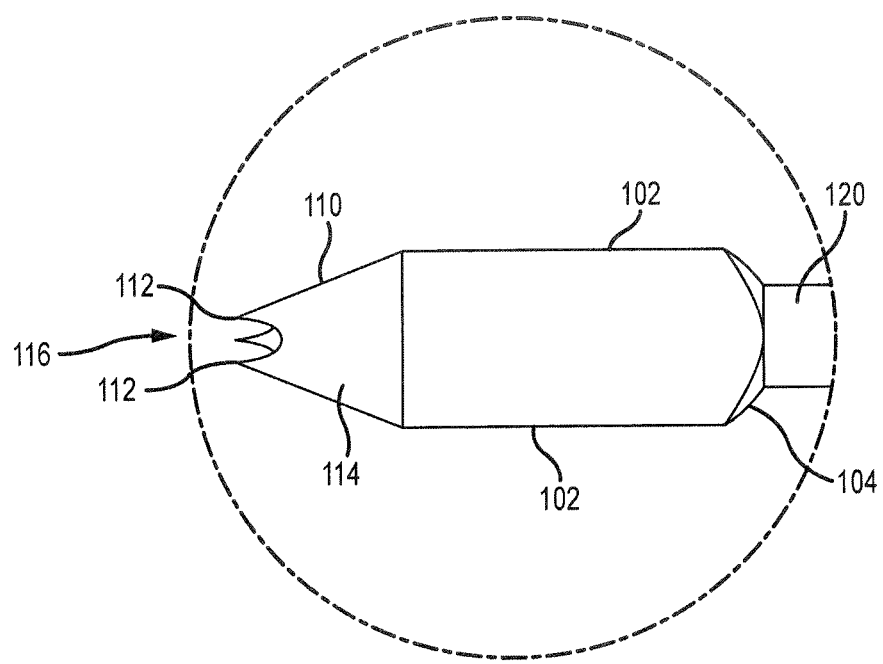
FIG. 5 illustrates a distal section of the tool according to aspects of the invention.
Figure 6:
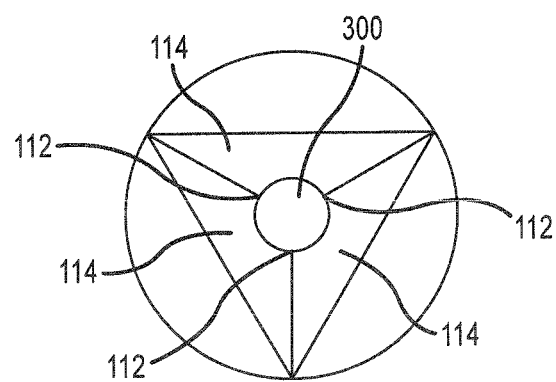
FIG. 6 is an end view of the distal tip of the distal section of a tool according to the invention.

The description of exemplary embodiments of the present invention provided below is merely exemplary and is intended for purposes of illustration only; the following description is not intended to limit the scope of the invention disclosed herein. Moreover, recitation of multiple embodiments having stated features is not intended to exclude other embodiments having additional features or other embodiments incorporating different combinations of the stated features.

The present disclosure describes medical tools and systems that are suitable for use in treatment of joints, and particularly for treatments including joint fusion or arthrodesis, such as arthrodesis of phalanges. For example, exemplary devices and systems described herein are suitable for treatment of a distal interphalangeal (DIP) joint, and other joints such as for fusion and the scrubbing of the joint prior to implantation of another device, such as a bone screw. The devices and systems are conveniently described below in connection with such treatment; however, unless otherwise noted, tools and systems described herein are not limited to such applications.

Turning now to the figures, FIGS. 1-4 illustrate a tool 10 in accordance with aspects of the invention. Tool 10 includes at least a proximal section 50 and a distal section 100, and preferably includes an intermediary section 200. In the illustrated example, a cannula 300 spans an interior length of tool 10. In accordance with other embodiments, cannula 300 spans at least a portion of tool 10. Cannula 300 can allow a portion of a guide wire, discussed in more detail below, to be received by at least a portion or all of tool 10.

Tool 10 can be used to remove cartilage or soften and/or break up marrow within a medullary cavity of a bone. The breaking up/softening of the marrow material can facilitate attachment of devices, such as screws or other forms of anchors, to the bone. Removal of cartilage from a joint can facilitate joint fusion In the illustrated example, proximal section 50 includes a section 52, a proximal tip 54, and a distal end 56. Proximal tip 54 can be configured to be received by a driver. Exemplary drivers include a variable or single speed electric drill. Proximal end 54 can also be configured to attach to a hand held driving device. Proximal tip 54 can be shaped as a truncated cone, with a portion of cannula 300 spanning at least partially, and in some cases, entirely through proximal tip 54. The truncated conical shape can facilitate insertion of proximal tip 54 into the driver. Distal end 56 can include a tapered section 60—e.g., in the form of a truncated cone, wherein a distal end 62 of tapered section 60 has a width that is less than a width of section 52. Section 52 can include a cylindrical or other suitable shape. A driver can engage section 52 to cause tool 10 to rotate about an axis A. A length of proximal section 50 can be about 30 percent or more, about 40 percent or more, or about 50 percent of more of the total length of the tool. A length of proximal section 50 can range from, for example, about 20 to about 30 mm, about 15 to about 40 mm, or about 10 to about 50 mm. A width of proximal section 50 can range from about 2 to about 4 mm, about 2 to about 6 mm, or be about 3.18 mm.

Distal section 100 includes one or more scraping surfaces 102 to scrape material within a medullary cavity of a bone or joint cavity. Scraping surface 102 can be formed at one or more edges of a portion of distal section 100. In the illustrated example, surfaces 108 of distal end 100 form a triangular prism, having a plurality, namely three edges that form scraping surface 102. In this case, a cross section of the portion of distal section 100 that scrapes or scrubs the medullary cavity or joint cavity has a triangular cross section. Other cross sections, such as square and other polygonal shapes, or overall flat shapes are also contemplated by this disclosure. A proximal end of distal section 100 can be tapered, as illustrated, to form a transition area between intermediary section 200 and surfaces 108 and edges 102. Distal section 100 can include any suitable number of scraping surfaces 102. By way of example, distal section 100 includes 1, 2, 3, 4, 5, 6, 7, or 8 or more scraping surfaces. A length of scraping surfaces 102, from proximal end 104 to a distal end 106 can range from about 5 to 6 mm, about 4 to 7 mm, or be about 5.09 mm. The width and length will vary and be relative to the joint cavity contemplated. For instance, for larger joints of the foot, a larger device is contemplated. A width of the scraping surface 102 of distal end 100 can be the same as the width of proximal section 50.

Distal section 100 can also include a head or tip 110 including one or more cutting surfaces 112. In the illustrated example, head 110 includes three cutting surfaces 112. Head 110 can be tapered from a relatively large width at a proximal end 118 (e.g., a width of scraping surfaces 102) to a distal end 116 (a width of cutting surfaces 112). For example, as shown in FIG. 5, head 110 can include one or more surfaces 114 that are tapered at an angle of about twenty degrees, or from about ten to about 30 degrees, or from about 5 to about 45 degrees. Cutting surfaces 112 can be further sharpened. In the illustrated example, head 110 has a pyramidal shape, with surfaces 114 that terminate at distal end 116 of cannula 300 and at proximal end 118 at distal end 106 of scraping surfaces 102 and surfaces 108. In this case, cutting surfaces 112 include a triangular shape. A length of head 110 can range from about 0.5 to about 10 mm, about 2 to about 8 mm, or be about 2.61 mm.

Intermediary section 200 spans between proximal section 50 and distal section 100. More particularly, intermediary section 200 can span between proximal end 104 of distal section 100 and distal end 56 of proximal section 50. Intermediary section 200 can be in the form of a cylinder. A width (e.g., outer diameter) of intermediary section 200 can be less than a width of distal section 100 and/or less than a width of proximal section 50. By way of examples, a width of intermediary section 200 ranges from about 1 mm to 3 mm, about 1 mm to 2 mm, or be about 1.57 mm. A length of intermediary section can range from about 2 to 25 mm, about 5 to 20 mm, or be about 12.64 mm.

As noted above, cannula 300 can extend through the entire length of tool 10. A diameter of cannula 300 can range from about 0.25 to 1 mm, about 0.5 to 1 mm, or be about 0.75 mm. The cannula can be configured to receive a guide wire, such as a 0.025" K-wire. The guide wire can be used to guide tool 10 into and through a medullary cavity. In some forms, the device may not have an internal cannula.

Tool 10 and sections 50, 100, and 200 can be formed of a variety of materials. By way of example, tool 10 is formed of 304 stainless steel. Tool 10 can be of unitary construction, or can be formed of multiple sections. For example, distal section 100 (e.g., a tip 120 of distal section 100) can be attachable to intermediary section 200 (e.g., to distal end 204 of intermediary section 200). Similarly, intermediary section 200 can be attachable (e.g., threadingly engaged) at a proximal end 202 to distal end 56 of proximal section 50. An overall length of tool 10 can range from about 25 to 75 mm, about 40 to about 60 mm, or be about 47.4 mm.

To use tool 10, a guide wire can be inserted into a medullary cavity to be scrubbed. Tool 10, which can be fitted onto a driver, can be inserted over the guide wire. The driver can be used to push tool 10 over the guide wire and into the medullary or joint cavity. The driver can further cause tool 10 to rotate and/or move along an axis of the medullary cavity, thereby causing a scraping (with surfaces 102) and cutting (with surface 112) of marrow material within the medullary cavity.

Non-limiting specific examples of devices according to the invention follow:

1. A tool for scrubbing the medullary cavity of a bone or joint cavity, the tool comprising a body having:
    (a) a distal section having a scraping surface to scrape a medullary cavity in order to soften marrow within the medullary cavity;
    (b) a proximal section; and
    (c) a cannula extending through the tool.
2. A tool for scrubbing the medullary cavity or joint of a bone, the tool comprising a body having:
    (a) a distal section having one or more cutting surfaces to soften marrow within a medullary cavity or remove cartilage and cortical bone from a joint cavity;
    (b) a proximal section; and
    (c) a cannula extending through at least a portion of the tool.
3. The tool of any of examples 1-2 wherein the proximal section has a proximal tip, and the proximal tip is connectable to a drill.
4. The tool of any of examples 1-3 wherein the proximal section is cylindrical.
5. The tool of any of examples 1-4 wherein the proximal section has a proximal width and the distal section has a distal width and the proximal width is equal the distal width.
6. The tool of any of examples 1-5 wherein the tool has a tool length and a length of the proximal section is at least 30% of the tool length.

7. The tool of any of examples 1, 3-6 wherein the scraping surface comprises an edge formed on the outer surface of the distal end.
8. The tool of any of examples 1, 3-7 wherein the scraping surface comprises a plurality of edges formed on the distal section.
9. The tool of any of examples 1, 3-8 wherein the portion of the distal section that scrubs the medullary cavity comprises a triangular cross section and three edges.
10. The tool of any of examples 1-9 that further includes an intermediary section between the proximal section and the distal section.
11. The tool of example 10 wherein the intermediary section has an intermediary width, and the intermediary width is less than a width of the proximal section or less than a width of the distal section.
12. The tool of any of examples 10-11 wherein the intermediary section is cylindrical.
13. The tool of any of examples 1-12 wherein the distal section includes a distal tip with at least one cutting surface.
14. The tool of example 13 wherein the distal tip has three cutting surfaces.
15. The tool of any of examples 1-14 that is one piece.
16. The tool of any of examples 1-14 wherein the distal section is attachable to the intermediary section.
17. The tool of example 15 wherein the distal section has a distal tip and a proximal end, and the proximal end is configured to be received in a distal end of the intermediary section.
18. The tool of any of examples 13-17 wherein the distal tip is a structure that narrows in width from a scraping surface to the cutting surface.
19. The tool of example 17 wherein the distal tip is triangular and has three proximal surfaces, wherein each proximal surface terminates in a triangular cutting surface.
20. A system including the tool of any of examples 1-19 and a driver.

Having thus described preferred embodiments of the invention, other variations and embodiments that do not depart from the spirit of the invention will become apparent to those skilled in the art. For example, while an exemplary tool has been described above in connection with scrubbing a medullary cavity of a phalange or joint cavity of a digit or appendage, the invention is not so limited. The scope of the present invention is not limited to any particular embodiment, but is instead set forth in the appended claims and the legal equivalents thereof. Further, unless expressly stated in the written description or claims, the steps of any method recited in the claims may be performed in any order capable of yielding the desired result.

What is claimed is:

1. A tool for scrubbing a medullary cavity of a bone or joint cavity, the tool comprising a body comprising:
   (a) a distal section having a scraping surface to scrape a medullary cavity or joint cavity in order to soften tissue within the medullary cavity or joint cavity, wherein the scraping surface is formed on the distal section and comprises a triangular cross section with three edges;
   (b) a proximal section having a proximal tip configured to be connectable to a drill;
   (c) a cannula extending through the tool; and
   (d) an intermediary section between the distal section and the proximal section, the intermediary section connected to the distal section and to the proximal section.
2. The tool of claim 1 wherein the proximal section is cylindrical.
3. The tool of claim 1 wherein the proximal section has a proximal width and the distal section has a distal width and the proximal width is equal to the distal width.
4. The tool of claim 1 wherein the tool has a tool length and a length of the proximal section is at least 30% of the tool length.
5. The tool of claim 1, wherein the intermediary section has an intermediary width, and the intermediary width is less than a width of the proximal section and less than a width of the distal section.
6. The tool of claim 1, wherein the intermediary section is cylindrical.
7. The tool of claim 1 wherein the distal section further includes a distal tip with at least one cutting surface.
8. The tool of claim 7, wherein the distal tip is a structure that narrows in width from the scraping surface to the at least one cutting surface.
9. The tool of claim 8 wherein the distal tip is triangular and has three proximal surfaces, wherein each proximal surface terminates in a triangular cutting surface.
10. The tool of claim 1 that is one piece.
11. The tool of claim 1, wherein the distal section is attachable to the intermediary section.
12. The tool of claim 11 wherein the distal section has a distal tip and a proximal end, and the proximal end is configured to be received in a distal end of the intermediary section.
13. A system including the tool of claim 1 and a driver.
14. A tool for scrubbing a medullary cavity of a bone or joint cavity, the tool comprising a body having:
   (a) a distal section having a scraping surface to scrape a medullary cavity or joint cavity in order to soften tissue within the medullary cavity or joint cavity, wherein the scraping surface is one or more edges of the distal section;
   (b) a proximal section having a proximal tip configured to be connectable to a drill;
   (c) a cannula extending through the tool;
   (d) an intermediary section between the distal section and the proximal section, the intermediary section connected to the distal section and to the proximal section;
   (e) the distal section further including a distal tip, wherein the distal tip includes at least one cutting surface; and
   (f) the distal tip narrows in width from the scraping surface to the at least one cutting surface.
15. The tool of claim 14, wherein the proximal section is cylindrical.
16. The tool of claim 14, wherein the proximal section has a proximal width and the distal section has a distal width and the proximal width is equal to the distal width.
17. The tool of claim 14, wherein the tool has a tool length and a length of the proximal section is at least 30% of the tool length.
18. The tool of claim 14, wherein the intermediary section has an intermediary width, and the intermediary width is less than a width of the proximal section and less than a width of the distal section.
19. The tool of claim 14, wherein the intermediary section is cylindrical.
20. The tool of claim 14 that is one piece.
21. The tool of claim 14, wherein the distal section is attachable to the intermediary section.
22. The tool of claim 21, wherein the distal section has a proximal end, and the proximal end is configured to be received in a distal end of the intermediary section.

23. The tool of claim 14, wherein the distal tip is triangular and has three proximal surfaces, wherein each proximal surface terminates in a triangular cutting surface.

24. A system including the tool of claim 14 and a driver.

* * * * *

UNITED STATES PATENT AND TRADEMARK OFFICE
CERTIFICATE OF CORRECTION

PATENT NO. : 10,194,923 B2
APPLICATION NO. : 15/151252
DATED : February 5, 2019
INVENTOR(S) : Lloyd P. Champagne, Jozef Zoldos and Attila A. Hunson It is certified that error appears in the above-identified patent and that said Letters Patent is hereby corrected as shown below:

On the Title Page

The Inventor Name item (72) reading "Atilla A Hunson" should be changed to --Attila A. Hunson--.

Signed and Sealed this
Twenty-third Day of January, 2024

*Katherine Kelly Vidal*

Katherine Kelly Vidal
*Director of the United States Patent and Trademark Office*